United States Patent
Iwasaki

(10) Patent No.: US 7,497,871 B2
(45) Date of Patent: Mar. 3, 2009

(54) SIMPLE WARMTH-RETAINING ARTICLE AND A WARMTH-RETAINING CLOTH

(75) Inventor: Hirohumi Iwasaki, Ashiya (JP)

(73) Assignee: Asahi Kasei Fibers Corporation, Osaka-Shi (JP)

( * ) Notice: Subject to any disclaimer, the term of this patent is extended or adjusted under 35 U.S.C. 154(b) by 0 days.

(21) Appl. No.: 10/559,285

(22) PCT Filed: Jun. 4, 2004

(86) PCT No.: PCT/JP2004/008149

§ 371 (c)(1),
(2), (4) Date: Dec. 2, 2005

(87) PCT Pub. No.: WO2004/108031

PCT Pub. Date: Dec. 16, 2004

(65) Prior Publication Data

US 2006/0135016 A1    Jun. 22, 2006

(30) Foreign Application Priority Data

Jun. 4, 2003    (JP) .............................. 2003-159494

(51) Int. Cl.
*A61F 7/00* (2006.01)
*B32B 5/18* (2006.01)

(52) U.S. Cl. ...................... 607/108; 607/111; 607/114; 442/373

(58) Field of Classification Search ................ 607/107, 607/108, 111, 114
See application file for complete search history.

(56) References Cited

U.S. PATENT DOCUMENTS

| | | | |
|---|---|---|---|
| 5,879,378 A | 3/1999 | Usui | |
| 5,984,953 A | 11/1999 | Sabin et al. | |
| 6,893,453 B2 * | 5/2005 | Agarwal et al. | ............. 607/108 |

FOREIGN PATENT DOCUMENTS

| | | |
|---|---|---|
| CN | 1226944 A | 8/1999 |
| JP | 62-197955 | 12/1987 |
| JP | 63-8018 | 1/1988 |
| JP | 64-3619 | 1/1989 |
| JP | 02265545 A * | 4/1989 |
| JP | 3015597 | 6/1995 |
| JP | 09-313249 | 12/1997 |
| JP | 11-309045 | 11/1999 |
| WO | WO 02/36051 A1 | 5/2002 |

OTHER PUBLICATIONS

International Search Report.
English Abstract of Publication No. CN1310600, dated Aug. 29, 2001.

* cited by examiner

*Primary Examiner*—Lynda Salvatore
(74) *Attorney, Agent, or Firm*—Finnegan, Henderson, Farabow, Garrett & Dunner, L.L.P.

(57) ABSTRACT

A simple warmth-retaining article comprising a heat insulating material, a cover material and an exothermic article that generates heat in the presence of air and that is inserted between the heat insulating material and the cover material, and a warmth-retaining cloth formed by connecting a plurality of the simple warmth-retaining articles in a plane-like state.

4 Claims, 1 Drawing Sheet

SIMPLE WARMTH-RETAINING ARTICLE AND A WARMTH-RETAINING CLOTH

FIELD OF THE INVENTION

The present invention relates to a lightweight, compact and simple warmth-retaining article and a warmth-retaining cloth for which the simple warmth-retaining article is used. The warmth-retaining cloth can, for example, wrap a human body, and it is particularly excellent in portability.

BACKGROUND ART

A disposable body warmer has often been used as an article for warming a part of a human body. Moreover, a body warmer, or the like, is used by affixing it to a painful portion such as a joint to partially warm a human body. The body warmer is suitable for locally warming a small portion such as a hand, a foot or a waist. However, it cannot warm a human body as a whole.

Japanese Unexamined Patent Publication (Kokai) No. 11-216157 discloses a packaging bag in which a plurality of air-permeable inner bags each containing an exothermic composition generating heat when contacted with oxygen in the air are collectively contained and that is excellent in airtightness. However, the patent publication only discloses that a plurality of exothermic articles each containing an exothermic composition are contained.

Japanese Unexamined Patent Publication (Kokai) No. 7-59809 discloses a sheet-like exothermic article formed by making a support that is composed of a nonwoven fabric of a water-absorbing fiber hold an exothermic composition that generates heat when contacted with air. However, the sheet-like exothermic article is one prepared by making a support of a nonwoven fabric hold an exothermic composition in an amount of 500 to 10,000 g and thermocompressing the support to become flat, and is characterized in that an optionally shaped sheet is cut out of the exothermic article and used.

Japanese Unexamined Patent Publication (Kokai) No. 7-112006 discloses a sticky exothermic article that includes a base sheet having on one side an adhesive applied to the base sheet and, on the other side, an exothermic container bag that is composed of an air-permeable wrapping material, and an exothermic agent that generates heat in the presence of air and that is contained in the exothermic container bag. Because the sticky exothermic article has an applied hot melt type adhesive, the article can be simply attached. However, the adhesive strength varies depending on the environmental temperature, and a problem, that the sticky exothermic article is hard to use at low environmental temperature, arises.

Japanese Unexamined Utility Model Publication (Kokai) No. 62-197955 discloses a warmth-retaining Japanese cushion. In the Utility Model Publication, an exothermic article inserted in a pocket on the warmth-retaining side is described. It is also described that the Japanese cushion side is an open-cell type cushioning material, and that the cushioning material is compactly vacuum packaged. However, an object of the utility model publication is to provide a Japanese cushion as a cushioning material and is not to provide a warmth-retaining cloth.

DISCLOSURE OF THE INVENTION

The problem of the present invention is to provide a simple warmth-retaining article that is compact, portable and convenient for carrying, that can be used by simple operation when required, during its use, that can be well attached to a human body, and that shows an excellent warmth retention at a suitable temperature for a long time, and also to provide a warmth-retaining cloth for which the simple warmth-retaining article is used.

As a result of intensively carrying out investigations to solve the above problem, the present inventors have achieved the present invention.

That is, the present invention is as explained below.

1. A simple warmth-retaining article comprising a heat insulating material, a cover material and an exothermic article that generates heat in the presence of air and that is inserted between the heat insulating material and the cover material.

2. The simple warmth-retaining article according to 1 described above, wherein the heat insulating material is a nonwoven fabric or a resin foam having a thickness of 0.2 to 20.0 mm, a weight of 30 to 700 g/m² and a void ratio of 40 to 95%.

3. The simple warmth-retaining article according to 1 or 2 described above, wherein the cover material is a nonwoven fabric or a fabric having a thickness of 0.05 to 0.5 mm and a fabric weight of 20 to 100 g/m².

4. The simple warmth-retaining article according to any one of 1 to 3 described above, wherein the edges of the heat insulating material and those of the cover material are bonded together by hot melt sticking or sewing.

5. The simple warmth-retaining article according to any one of 1 to 4 described above, wherein the exothermic article is contained in a packaging bag, and the packaging bag has continuous lattice-like partitions.

6. The simple warmth-retaining article according to 3 described above, wherein the nonwoven fabric is a nonwoven fabric of a thermoplastic synthetic filaments yarn having a partial thermocompression ratio of 3 to 35%.

7. The simple warmth-retaining article according to 3 described above, wherein the fabric is a woven fabric, a knitted fabric, a cheesecloth or an extruded mesh or net.

8. A simple warmth-retaining article formed by packaging and sealing the simple warmth-retaining article according to any one of 1 to 7 described above with a non-air-permeable film external bag while the warmth-retaining article is in a deaerated or deoxidized state.

9. A warmth-retaining cloth formed by connecting a plurality of the simple warmth-retaining articles according to any one of 1 to 7 described above, in a plane-like state.

10. The warmth-retaining cloth according to 9 described above, wherein the warmth-retaining cloth is packaged and sealed with a non-air-permeable film external bag while the warmth-retaining cloth is in a deaerated or deoxidized state.

11. The warmth-retaining cloth according to 9 or 10 described above, wherein the warmth-retaining cloth has a jig capable of attaching or detaching, in the outer layer, a mat that has thermal reflectivity.

The present invention is explained below in detail.

The warmth-retaining article of the present invention is an article in which an exothermic article that generates heat in the presence of air is inserted between a heat insulating material excellent in heat insulation and warmth retaining and a cover material that is thin and excellent in heat conductivity; an object can be warmed and warmth retained by contacting the side of the cover material of the simple warmth-retaining article with the object (see FIG. 1). Because the exothermic article generates heat in the presence of air, it must be stored while the air (oxygen) is being shielded before use. Accordingly, the warmth-retaining article is preferably sealed with a non-air-permeable film external bag and packaged while the warmth-retaining article is in a deaerated or deoxidized state (see FIG. 2).

In the present invention, there is no specific limitation on the insulating material as long as it is bulky, flexible, heat insulating and excellent in strength. However, a resin foam, a nonwoven fabric, and the like, excellent in heat insulation, flexibility, a cushioning property, and the like, are preferred.

The heat insulating material has a thickness of preferably 0.2 to 20 mm, more preferably 0.3 to 15 mm, a weight of preferably 30 to 700 g/m$^2$, more preferably 50 to 500 g/m$^2$. When the thickness is 0.2 mm or more, and the weight is 30 g/m$^2$ or more, the warmth-retaining article has a suitable thickness, and is excellent in bulkiness, heat insulation and warmth retention. Moreover, when the thickness is 20 mm or less, and the weight is 700 g/m$^2$ or less, the heat insulation material shows excellent flexibility as well as good heat insulation, and it can be made compact and ease to handle.

Because the heat insulating material becomes excellent in heat insulation and flexibility when it contains much air, it is preferred that the heat insulating material have a relatively large void ratio. The void ratio is preferably from 40 to 95%, more preferably from 50 to 97%. When the void ratio is in the above range, the air content is suitable, and the excellent flexibility and excellent heat insulation of the heat insulating material can be obtained; moreover, the heat insulating material becomes excellent in strength and handleability. In addition, the void ratio is defined by the following formula:

void ratio (%)=[1−$D_a/D_0$]×100 wherein $D_a$ represents an average apparent density, and $D_0$ represents a resin density.

Moreover, as means for further improving the heat insulation effect by preventing heat radiation of the heat insulating material, for example, the inner side of the heat insulating material (namely, exothermic article side) is sputtered with a metal, or a vapor deposition film such as an aluminum vapor deposition film is applied to the inner side.

Preferred examples of the resin foam used as the heat insulating material include foams such as a polyurethane resin, a synthetic rubber resin, a polyethylene resin and a polystyrene resin. In particular, a urethane foam excellent in resilience or a laminated article of a resin foam and a nonwoven fabric is preferably used.

A nonwoven fabric preferably used as the heat insulating material is preferably high in bulkiness. Examples of the fiber forming the nonwoven fabric include fiber of olefin substances such as polyethylene, polypropylene and copolymerized polypropylene, fiber of polyamide such as nylon 6 and nylon 66, fiber of polyester such as poly(ethylene terephthalate), poly(butylene terephthalate), copolymerized polyester and aliphatic polyester. Alternatively, examples thereof include thermoplastic synthetic fiber such as a composite fiber having a core-sheath structure wherein the sheath is formed out of polyethylene, polypropylene, copolymerized polyester, or the like, and the core is formed out of polypropylene, poly(ethylene terephthalate), or the like, acrylic fiber, rayon fiber, natural fiber such as cotton, hemp, wool, or the like. Such short fibers or filaments yarns may be used singly, or at least two of them may be used in combination.

The nonwoven fabric preferably used as the heat insulating material can be obtained by processing a web of such a fiber by a known method such as a spun bonding method, a carding method or an air laying method. Moreover, the fiber web can also be processed by a known bonding method such as partial thermocompression bonding by which the fiber web is heat pressed with a heating emboss roll, or mechanical interlacing with a machine such as a needle punching machine. In particular, a nonwoven fabric of a synthetic filaments yarn obtained by machine interlacing such as needle punching is preferably used.

In addition, for the filaments yarn nonwoven fabric, the partial thermocompression bonding ratio is preferably from 3 to 35%. When the thermocompression bonding ratio is in the above range, the fiber web is well bonded to have an adequate strength, has a soft feeling, and is well contacted with an uneven shape.

In the present invention, the cover material is preferably a nonwoven fabric or a fabric that is flexible, thin and excellent in strength.

The cover material has a thickness of preferably 0.05 to 0.5 mm, more preferably 0.1 to 0.4 mm, a fabric weight of preferably 20 to 100 g/m$^2$, more preferably 25 to 80 g/m$^2$. When the cover material has a thickness of 0.05 mm or more and a fabric weight of 20 g/m$^2$ or more, an adequate strength can be obtained. Moreover, when the thickness is 0.5 mm or less and the fabric weight is 100 g/m$^2$ or less, an excellent flexibility and an excellent A heat conductivity can be obtained.

Examples of the fiber forming the nonwoven fabric that is preferably used as the cover material include fiber of olefin substances such as polyethylene, polypropylene and copolymerized polypropylene, fiber of polyamide such as nylon 6 and nylon 66, fiber of polyester such as poly(ethylene terephthalate), poly(butylene terephthalate), copolymerized polyester and aliphatic polyester. Alternatively, examples thereof include a thermoplastic synthetic fiber such as a composite fiber having a core-sheath structure wherein the sheath is formed out of polyethylene, polypropylene, copolymerized polyester, or the like, and the core is formed out of polypropylene, poly(ethylene terephthalate), or the like, acrylic fiber, rayon fiber, natural fiber such as cotton, hemp, wool, or the like. Such short fibers or filaments yarns may be used singly, or at least two of them may be used in combination.

The nonwoven fabric preferably used as the cover material can be obtained by processing a web of such a fiber by a known method such as a spun bonding method, a carding method or an air laying method. Moreover, the fiber web can also be processed by a known bonding method such as partial thermocompression bonding by which the fiber web is heat pressed with a heating emboss roll, mechanical interlacing with a machine such as a needle punching machine and fluid interlacing with a water needle, etc. In particular, a nonwoven fabric of a synthetic filament yarn that is obtained by a spunbond method and that is thin and excellent in strength is preferred.

The average yarn diameter of the fiber forming the nonwoven fabric that is preferably used as the cover material is preferably from 1 to 40 μm, more preferably from 10 to 30 μm. When the average yarn diameter is in the above range, the strength is sufficient, and the filaments are hardly broken. The yarn therefore shows good spinnability. The cover material has sufficient bulkiness and is excellent in flexibility, and the productivity is high.

The nonwoven fabric preferably used as the cover material is preferably a nonwoven fabric of a synthetic filaments yarn having a partial thermocompression bonding ratio of 3 to 35%. When the partial thermocompression bonding ratio is in the above range, the fiber web shows good bonding and a sufficient strength. Moreover, because the bonding is suitable, the nonwoven fabric has a soft feeling, and is well contacted with an uneven shape.

The nonwoven fabric preferably used as the cover material shows a tensile strength of preferably 20 N/5 cm or more, more preferably 30 N/5 cm or more. The nonwoven fabric having a tensile strength of 20 N/5 cm or more is not broken even when it is used for covering a person's body and the person is transferred. Moreover, the ratio of a tensile strength in the longitudinal direction to a tensile strength in the transverse direction of the above nonwoven fabric of a filament yarn is preferably from 0.7 to 3.5, more preferably from 0.9 to 3.0. When the fiber of the nonwoven fabric is uniformly dispersed, the trouble of breakage during handling hardly takes place. The uniform dispersion is therefore preferred.

Examples of the fabric preferably used as the cover material in the present invention include a woven fabric, a knitted fabric, a cheesecloth, an extruded mesh, a tape yarn cloth and a net. Examples of the fiber forming the fabric include a synthetic fiber of nylon, polyester, polyethylene or polypropylene, rayon fiber, natural fiber such as a rayon fiber cotton, hemp or wool. These fibers may be used singly, by blending or by combining.

The bending resistance of a nonwoven fabric or a fabric that is preferably used as the cover material is preferably 10 cm or less, more preferably 8 cm or less. That the bending resistance of the nonwoven fabric or fabric is small signifies that the nonwoven fabric or fabric has a soft feeling and flexibility, and that the nonwoven fabric or fabric is readily contacted with an uneven shape well. When the bending resistance is 10 cm or less, the nonwoven fabric or fabric has a soft feeling, and is readily contacted with an uneven shape well.

The exothermic article in the present invention is satisfactory as long as it generates heat in the presence of air, and a known material can be used therefor. Examples of the material include a composition mainly containing metal powder such as iron powder, water, an oxidation assistant such as sodium chloride and a water-retaining agent such as wood powder, vermiculite and activated carbon, and a composition mainly containing an alkali metal sulfide, a polysulfide, or hydrated salts of these substances and a carbonaceous substance and/or iron carbide.

In the present invention, the exothermic article is preferably contained in a packaging bag. In order that the exothermic article may be contacted with air (or oxygen), and generated heat readily and efficiently, the packaging bag preferably has a large air-permeability, and the air-permeability is preferably adjustable. A film having air permeable holes and a heat sealing property is preferred as a material used for the packaging bag. For example, a material obtained by laminating a reinforcing material such as a nonwoven fabric to a film having holes obtained by perforating a polyethylene film or a microporous film obtained by mixing a resin with an inorganic filling agent is a preferred example.

In addition, in order to increase the rate of the temperature rise of the warmth-retaining article at the initial stage of starting the use, the air-permeability of the packaging bag is preferably made relatively large. For example, the following are preferred: a size of each film hole of from 100 to 500 µm; and a number of holes of from 30 to 100 per circular area having a diameter of 2.86 cm. Moreover, the air-permeability is preferably from 0.5 to 10 sec/100 ml.

There is no specific restriction on the size and shape of the packaging bag, and the size and shape can be suitably selected according to the application.

When the exothermic article is a powdery material, it is preferably distributed in the packaging bag as uniformly as possible without unevenness. In order to uniformly arrange the powdery exothermic article, it is preferred to provide partitions in the packaging bag. There are no specific limitations on the shape, number, intervals (spaces), and the like, of the partitions, and they can be suitably selected according to the size and application of the packaging bag. Examples of the partitions include lattice-like ones, circular ones and shape-modified ones. Of these partitions, continuous lattice-like partitions are preferred. In the production line of the packaging bags of the exothermic article, continuous partitions or lattice-like partitions can be formed by omitting the slitting step and the cutting step for the packaging bags. Continuous partitions, or lattice-like partitions can be formed by effectively utilizing the step of producing the packaging bags of the exothermic article.

The partitions are preferably formed so that the housing portions of the exothermic article are each made as small as possible. One practically preferred example is as follows: rectangularly formed blocks (with partitions) each having a side of 5 to 10 cm and another side of 7 to 15 cm, and a powdery exothermic article being contained in an amount of 5 to 60 g per partition. The mass of the powdery material per block can be suitably determined while the whole weight, the warming performance, a warmth-retaining time, and the like, are being taken into consideration. For example, in order to shorten a warmth-retaining time, it is preferred to fill from 10 to 40 g of the exothermic article per block of the packaging material. Moreover, there is no specific restriction on the method of forming partitions. For example, a method of forming partitions by sewing or heat sealing can be employed.

A plurality of the simple warmth-retaining articles of the invention can be connected in a plane-like state to form a warmth-retaining cloth (see FIG. 3). In order to obtain a warmth-retaining cloth having such a shape, a plurality of the units of the simple warmth-retaining article units explained above may be connected by sewing, or the like procedure, in a plane-like state in the longitudinal and transverse directions. However, the warmth-retaining cloth is preferably prepared by the following procedure: using a heat insulating material and a cover material that have each a wide area like a blanket, a plurality of portions (blocks) where packaging bags of the exothermic articles are inserted are provided by forming blocks by sewing or the like procedure. There is no specific restriction on the means of forming the blocks, and heat sealing, ultrasonic sealing, impulse sealing, or the like procedure, may also be employed in addition to sewing.

When the warmth-retaining cloth is prepared, a wide area can be warmth-retained. When the object is a human body, it can be used widely, for example, the upper or lower half of a person's body or a person's body as a whole can be covered and warmth retained. The warmth-retaining cloth may also be, for example, a blanket-like fabric or a fabric sewn according to a clothing-like shape such as a gown-like shape. The size and shape are suitably selected according to the application, and there is no specific limitation thereon.

For a blanket-like fabric, for example, it has dimensions of about 25 to 160 cm (width)×about 30 to 220 cm (length), and a plurality of insertion portions for the packaging bags of the exothermic article are preferably provided. There is no specific restriction on the shape and size of each insertion portion for the packaging bags, and they can be suitably selected according to the application. The dimensions are preferably 1 to 5 cm larger than those of the packaging bag of the exothermic article.

One specific example is explained below. A sheet of a heat insulating material, 120 cm (width)×210 cm (length), and a sheet of a cover material having the same dimensions are prepared, and both sheets are stacked. The stacked sheets are bisected in the transverse direction, and trisected in the longitudinal direction. Six blocks are prepared by a known bonding procedure such as machine sewing, ultrasonic sewing or heat sealing. Six blocks each 50 to 55 cm wide and 60 to 65 cm long are prepared while a suitable interval about several centimeters wide is placed between two adjacent blocks. A packaging bag of the exothermic article 45 to 50 cm wide and 55 to 60 cm long is inserted into each block, and the resultant fabric can be used. Each packaging bag has preferably from 4 to 8 blocks, and each block is filled with 20 to 30 g of the exothermic article.

For a warmth-retaining cloth such as explained above, in order to repeatedly use the heat insulating material and the cover material by replacing the packaging bags of the exothermic articles after use, it is preferred to adopt, for example, the following procedure.

It is important that each block into which a packaging bag of an exothermic article is inserted stably hold the packaging bag without damage and without dropping the packaging bag outside during use. Sewing or heat sealing is therefore conducted to make the size of the insertion opening for the packaging bag smaller than the packaging bag by about 2 to 10 cm. Six packaging bags are each folded and inserted into the six blocks, respectively. As a result, the inserted packaging bags are hardly dropped or shifted even when the warmth-retaining cloth is folded or spread during use. Moreover, the insertion openings of the packaging bags are preferably provided on the side of the cover material. In order to prevent each packaging bag of the exothermic article from dropping outside, the following procedures are optionally taken preferably: providing a stopper such as a string, a button, a magic tape or a fastener to the insertion opening, or affixing a pressure sensitive adhesive double coated tape to a part of the packaging bag of the exothermic article; and the insertion opening for the packaging bag is closed with a double coated film or an adhesive tape.

In the present invention, because the exothermic article generates heat in the presence of air, it must be stored while air (oxygen) is being shielded before use. Accordingly, the exothermic article is preferably packaged and sealed in a degassed or deoxidized state during storage with a non-air-permeable-film external bag.

The non-air-permeable-film external bag is preferably a non-oxygen-permeable and gas-barriering film. Examples of the external film include an article coated with a poly(vinyl chloride) film, a poly(vinylidene chloride) film, a nylon film or a vinylidene chloride resin. When the exothermic article is stored while oxygen is being shielded with such a non-air-permeable film external bag, the exothermic reaction of the exothermic article is inhibited, and the consumption and deterioration thereof are prevented. As a result, the exothermic article can be stored for a long period. The interior of the simple warmth-retaining article that is packaged and sealed with an external bag is satisfactory as long as the exothermic article is in a state without contact with oxygen. For example, the interior should be in a degassed state or in a state of being filled with an inert gas such as nitrogen.

In particular, when the simple warmth-retaining article is used for a warmth-retaining cloth for rescuing, the simple warmth-retaining article is desirably in a compact form. In order to obtain a warmth-retaining article that is thin and compact so that it can be conveniently carried or be portable, the warmth-retaining article is preferably packaged with an external bag while air in the interior of the bag is being removed to be in a degassed state, and sealed while the interior is being evacuated. When the warmth-retaining article is treated in such a manner, the following effects are achieved: the cloth is compact during carrying, and a person can conveniently bear it; the exothermic article does not generate heat during carrying, and is safe; and heating or warmth retaining can be conducted during the use by an extremely simple operation. It can be said that the warmth-retaining article is particularly useful as a warmth-retaining cloth for rescue.

In particular, such a large and bulky warmth-retaining cloth as mentioned above is, during storage, folded or rolled. The air in the external bag is then removed, and the external bag is sealed while being in a degassed state. As a result, the warmth-retaining cloth becomes compact, and can be conveniently stored and carried. If necessary, the packaging bag of an exothermic article alone is sealed with a non-air-permeable film external bag. When used, the packaging bag of the exothermic article is taken out of the external bag to be inserted between the heat insulating material and the cover material.

The warmth-retaining cloth of the present invention formed as explained above readily generates heat by introducing air by breaking the non-air-permeable film external bag during use, and exhibits a warmth-retaining effect.

When a mat having heat reflectivity is used in the external layer (surface of the heat insulating material side) of the warmth-retaining cloth, in the present invention, the warmth-retaining property of the warmth-retaining cloth is further improved, and the cloth can retain warmth for a long time. For example, one preferred embodiment of the mat is a mat or a sheet having a deposition coating of metal such as aluminum on the surface. In order to use the mat or sheet, a jig capable of attaching a mat having heat reflectivity to the external layer of the warmth-retaining cloth or removing the mat therefrom is preferably prepared.

Because the simple warmth-retaining article and the warmth-retaining cloth of the present invention are convenient for storing or carrying, they are useful as warmth-retaining articles for a sick or a wounded person in an emergency. For example, in the case of rescuing a victim in a snowy mountain, the victim's whole body is covered with the warmth-retaining cloth of the invention, and the victim can be subjected to warmth-retaining treatment at 40 to 50° C. for 3 to 24 hours.

An antibacterial or bacteria-free material is preferred as the heat insulating material or the cover material in application for use on sick or wounded persons, or the like. Examples of the procedure for imparting antibacterial properties include a procedure comprising adding an antibacterial agent such as silver-ceramic to a resin, and fiberizing the resin, and a procedure comprising coating the materials with an antibacterial agent such as polylysine, chitosan, paraben, or the like. A nonwoven fabric having a laminated extremely fine fiber web as an intermediate layer is effective as a bacteria-free material.

The simple warmth-retaining article and the warmth-retaining cloth are preferably subjected to sterilization treatment. For example, they are preferably formed out of materials that can be sterilized with an ethylene oxide gas, an electron beam, a gamma ray, or the like. Alternatively, they are preferably formed out of materials that can be sterilized with an autoclave. Moreover, in view of the design of simple warmth-retaining article and the warmth-retaining cloth, the heat insulating material, the cover material, and the like, are preferably colored with a complementary color using a pigment, a dye, etc., or by printing, or the like procedure so that blood, etc., does not become conspicuous. Although the fabric can be colored by printing or dyeing by a known method, a method of adding a coloring agent to a resin and obtaining a colored fiber therefrom is preferred because the method can be conducted at low cost and the fastness of the color of the fabric is excellent.

Figure 1:
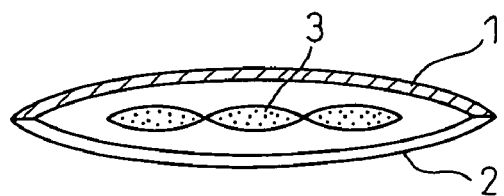
FIG. 1 is a cross-sectional view schematically showing one embodiment of a simple warmth-retaining article of the present invention.
Figure 2:
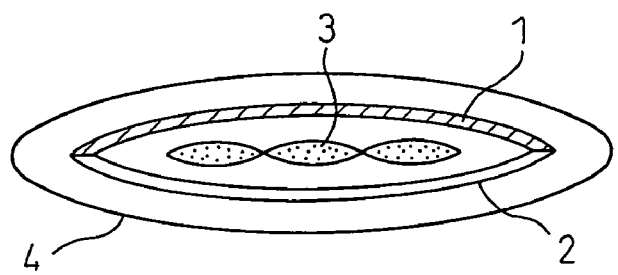
FIG. 2 is a cross-sectional view schematically showing one embodiment of a simple warmth-retaining article that is prepared by packaging a simple warmth-retaining article of the present invention with a non-air-permeable film external bag and sealing the film external bag.
Figure 3:
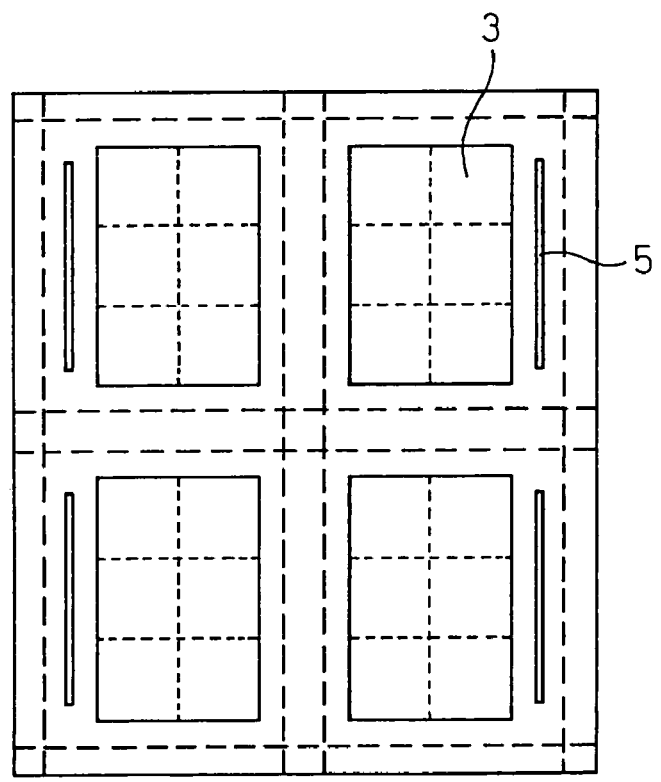
FIG. 3 is a plan view schematically showing one embodiment of a warmth-retaining cloth prepared by connecting a plurality of simple warmth-retaining articles of the present invention.

BRIEF DESCRIPTION OF REFERENCE NUMERALS 1 heat insulating material
2 cover material
3 packaging bag of an exothermic article
4 non-air-permeable film external bag
5 insertion opening of a packaging bag of an exothermic article

BEST MODE FOR CARRYING OUT THE INVENTION

The present invention is explained below in more detail by making reference to examples. However, the present invention is in no way restricted thereto.

In addition, measurement methods, and the like, in the examples are as explained below.

(1) Fabric Weight (g/m$^2$)

Measurements are made in accordance with JIS L 1906. Three samples each having dimensions of 20 cm (length)×25 cm (width) are cut out. The mass of each sample is measured, and the average value per unit area is determined.

(2) Thickness (mm)

Measurements are made under a load of 2 kPa in accordance with JIS L 1906.

(3) Average Yarn Diameter (μm)

A yarn is photographed with a magnification ×500, and the diameter is determined. The average yarn diameter is obtained from 10 sample yarns.

(4) Tensile Strength (N/5 cm)

A sample, 5 cm (width)×30 cm (length), is cut out, and the tensile strength of the sample is measured at a tensile speed of 10 cm/min using a tensile testing machine, with a chuck-to-chuck distance of 20 cm. Three samples in the longitudinal direction and three samples in the transverse direction are used, and the average values, in both directions, are obtained.

(5) Average Apparent Density (g/cm$^3$)

The average apparent density of a sample is obtained from the following formula:

average apparent density=(fabric weight)/(thickness)

(6) Bending Resistance (cm)

The bending resistance of a sample is determined by 45 degree cantilever method in accordance with JIS L 1906 in both the longitudinal and the transverse direction.

EXAMPLE 1

A nonwoven fabric of a synthetic fiber nylon filaments yarn that was prepared by a known spun bonding method and that had a thickness of 0.22 mm, a fabric weight of 50 g/m$^2$, an average yarn diameter of 16 μm, a void ratio of 80%, a bending resistance of 3.5 cm in the longitudinal direction and 2.3 cm in the transverse direction and a partial thermocompression bonding ratio of 11% was used as a cover material.

A nonwoven fabric of a synthetic fiber nylon filaments yarn that was prepared by a known spun bonding method and that had a thickness of 0.67 mm, a fabric weight of 100 g/m$^2$, an average yarn diameter of 14 μm, a void ratio of 83%, a bending resistance of 5.4 cm in the longitudinal direction and 3.7 cm in the transverse direction and a partial thermocompression bonding ratio of 5% was used as a heat insulating material.

A sheet material 90 cm wide and 180 cm long was cut out of the above cover material, and a sheet material having the same dimensions was cut out of the above heat insulating material. Both sheet materials were stacked. One partition bisecting the central portion in the transverse direction was formed by machine sewing, and two partitions trisecting the central portion in the longitudinal direction were formed by machine sewing to give a blanket having six bag-shaped blocks into which packaging bags of an exothermic article could be inserted. Six packaging bags of an exothermic article (iron powder, moisture, charcoal, vermiculite and salt) that was to exothermically react with oxygen in the air were inserted into the six bag-shaped blocks of the blanket, respectively, with each block formed from the cover material and the heat insulating material. As a result, a warmth-retaining cloth in which a plurality of the simple warmth-retaining articles of the present invention were connected was obtained. In addition, each packaging bag of the exothermic article had 16 blocks formed by 4 lines in the longitudinal direction and 4 rows in the transverse direction, and each block was filled with 10 g of an exothermic article.

Magic Tape (trade name) was attached to four end portions of the blanket so that the blanket could be fixed to a human body after covering it therewith. The blanket was then folded so that the folded blanket had dimensions of about 45 cm (width)×about 25 cm (length)×about 7 cm (height). The folded blanket was packaged with a non-air-permeable nylon film while being in a degassed state, and stored.

In order to use the warmth-retaining cloth, the non-air-permeable nylon film of the external bag was broken and spread, and the warmth-retaining cloth was spread. The front side of a human body was covered with the warmth-retaining cloth. The blanket temperature was 40° C. 10 minutes after starting the use, and 45° C. 20 minutes after starting the use. The human body could be warmth retained for about 6 hours at blanket temperatures of 40 to 45° C.

EXAMPLE 2

A nonwoven fabric of a synthetic fiber polyester filaments yarn that was prepared by a known spun bonding method and that had a thickness of 0.15 mm, a fabric weight of 30 g/m$^2$, an average yarn diameter of 14 μm, a void ratio of 86%, a bending resistance of 4.5 cm in the longitudinal direction and 3.8 cm in the transverse direction and a partial thermocompression bonding ratio of 15% was used as a cover material.

A card web of a polyester short fiber having a fabric weight of 150 g/m$^2$ was laminated to a nonwoven fabric of a synthetic fiber polyester filaments yarn that was prepared by a known spun bonding method and that had a fabric weight of 50 g/m$^2$.

The laminated material was mechanically interlaced by needle punching 80 times/cm² on both sides with a No. 36 regular type needle. The resultant material was used as a heat insulating one. The heat insulating material had a thickness of 3.5 mm, a fabric weight of 200 g/m², an average yarn diameter of 14 µm and 20 µm, a void ratio of 93%, a bending resistance of 7.5 cm in the longitudinal direction and 5.8 cm in the transverse direction.

A sheet material 120 cm wide and 210 cm long was cut out of the above cover material, and a sheet material having the same dimensions was cut out of the above heat insulating material. Both sheet materials were stacked. One longitudinal line 5 cm apart from one edge in the transverse direction and another longitudinal line 5 cm inwardly apart from the other edge in the transverse direction, and two longitudinal lines about 10 cm apart from each other in the longitudinal central portion were each machine sewn. One transverse line 5 cm inwardly apart from one edge in the longitudinal direction was machine sewn. A bag-shaped blanket in which 2 packaging bags of an exothermic article could be separately contained was thus prepared.

Two packaging bags of the exothermic article were inserted between the cover material and the heat insulating material from the other edge (not sewn) in the longitudinal direction of the blanket so that each block thus formed contained one packaging bag. A warmth-retaining cloth in which a plurality of the simple warmth-retaining articles of the present invention were connected was thus obtained. As a result of using the warmth-retaining cloth for covering a human body as a whole with the warmth-retaining cloth, the blanket had a temperature of 40° C. 13 minutes after starting the use, and a maximum temperature of 48° C. The human body could be warmth retained for about 10 hours at blanket temperatures of 40 to 48° C.

In addition, lattice-like partitions were formed in each packaging bag of the exothermic article so that the packaging bag had 30 blocks (2 rows in the transverse direction and 15 lines in the longitudinal direction), and each block was filled with 15 g of an exothermic article (iron powder, moisture, charcoal, vermiculite and salt). The packaging bag was packaged with a polypropylene film having been coated with a non-air-permeable vinylidene chloride resin in advance and sealed. The sealed packaging bags thus obtained were stored. When the packaging bags were to be used, the seals were broken, and the packaging bags were inserted in the blanket. Moreover, in order to fix the blanket after covering a human body, three pieces of string were attached to three parts of the blanket (both edges and the central part of the blanket), respectively.

EXAMPLE 3

A nonwoven fabric of a synthetic fiber polypropylene filaments yarn that was prepared by a known spun bonding method and that had a thickness of 0.18 mm, a fabric weight of 30 g/m², an average yarn diameter of 20 µm, a void ratio of 83%, a bending resistance of 4.5 cm in the longitudinal direction and 3.8 cm in the transverse direction and a partial compression bonding ratio of 25% was used as a cover material.

A nonwoven fabric of a synthetic fiber nylon filaments yarn that was prepared by a known spun bonding method and that had a thickness of 0.25 mm, a fabric weight of 50 g/m², an average yarn diameter of 13 µm, a void ratio of 87%, a bending resistance of 3.6 cm in the longitudinal direction and 3.2 cm in the transverse direction and a partial compression bonding ratio of 11% was used as a heat insulating material (in addition, a green pigment was added to a nylon polymer (the starting material of the nonwoven fabric) in an amount of 3 wt. %).

A sheet, 90 cm (width)×100 cm (length), was cut out of the cover material, and a sheet having the same dimensions was cut out of the heat insulating material. Both sheets were stacked, and sewn as explained below to form a bag shape. Two lines each 17 cm inwardly apart from the edge in the transverse direction were sewn, and the centerline of both edges was sewn. In the longitudinal direction, the following were each sewn: a portion folded back along a line inwardly apart from the upper edge, a portion 15.5 cm inwardly apart from the lower edge, and portions trisecting the central portion. The packaging bags of an exothermic article were to be inserted from both edges, and a lap margin of 5 cm was taken and sewing was conducted. Moreover, the periphery was sewn with an overlock machine, and others were lock stitched. That is, 6 blocks that were each to contain one packaging bag of an exothermic article were provided. Each block had a width of 28 cm and a length of 21.5 cm.

A packaging bag was prepared by laminating a perforated low density polyethylene film to a nonwoven fabric of a nylon filaments yarn having a thickness of 0.22 mm and a fabric weight of 40 g/m². The packaging bag thus obtained was filled with an exothermic article (iron powder, moisture, charcoal, vermiculite and salt) in an amount of 25 g/m². The packaging bag, 26 cm (width)×20 cm (length), had a 4 block structure (showing a decreased uneven distribution of the exothermic article) by forming bisecting partitions in both the transverse and the longitudinal direction.

The warmth-retaining cloth thus obtained was folded to form a small packing, 21 cm (width)×28 cm (length)×4 cm (height). The small packing was packaged with an external bag of a polypropylene film coated with a vinylidene chloride resin to give a package having a weight of 730 g.

In order to use the warmth-retaining cloth, the external bag was broken and the warmth-retaining cloth was spread. The whole of a human body was covered therewith. A polyethylene foam resin mat 5 mm thick having an aluminum coating formed by vapor deposition was used on the outer surface side of the heat insulating material. As a result, the warmth-retaining cloth had a temperature of 40° C. 10 minutes after starting the use, and a maximum temperature of 50° C., and the human body could be warmth retained at blanket temperatures of 40 to 50° C. for 12 hours.

In addition, when the mat was not used, the warmth-retaining cloth had a temperature of 40° C. 13 minutes after starting the use, and a maximum temperature of 45° C. The human body could be warmth-retained at blanket temperatures of 40 to 45° C. for 7 hours.

INDUSTRIAL APPLICABILITY

The simple warmth-retaining article of the present invention comprises a heat insulating material excellent in flexibility, heat insulation, and the like, a cover material, and an exothermic article that generates heat in the presence of air. Because the simple warmth-retaining article is lightweight and compact during storage or carrying, it can be conveniently carried or borne, and it is safe. The use of electricity or a generator is not necessary when the warmth-retaining article is used, and a simple operation can prepare a warmth-retaining blanket (warmth-retaining cloth) that can warmth-retain even a large area at suitable temperatures for a given time.

Accordingly, in case of an emergency where warmth retention is required, for example, a sick person, a victim, or the like, in the sea or a mountain area, can be readily warmth-retained at blanket temperatures of 40 to 50° C. for 3 to 24 hours. The simple warmth-retaining article is therefore useful as a warmth-retaining article or a warmth-retaining cloth for an emergency rescue.

The invention claimed is:

1. A warmth-retaining cloth useful for emergency rescue comprising a plurality of simple warmth-retaining articles connected together in a plane-like state, wherein the simple warmth-retaining articles comprise a heat insulating material, a cover material and an exothermic article that generates heat in the presence of air and that is inserted between the heat insulating material and the cover material, the heat insulating material being a nonwoven fabric or a resin foam having a thickness of 0.2 to 20.0 mm, a fabric weight of 30 to 700 g/m$^2$ and a void ratio of 40 to 95%, and the cover material being a nonwoven fabric or a fabric having a thickness of 0.05 to 0.5 mm and a fabric weight of 20 to 100 g/m$^2$, wherein the exothermic article is contained in a packaging bag, and the packaging bag has continuous lattice-like partitions, the warmth-retaining cloth has a blanket-like shape and has dimensions of 25 to 160 cm (width) and 30 to 220 cm (length), and is packaged and sealed within a non-air-permeable film external bag while the warmth-retaining cloth is in a deaerated or deoxidized state.

2. The warmth-retaining cloth according to claim 1, wherein edges of the heat insulating material and those of the cover material are bonded together by hot melt sticking or sewing.

3. The warmth-retaining cloth according to claim 1 or 2, wherein the nonwoven fabric of the cover material is a nonwoven fabric of a thermoplastic synthetic filament yarn having a partial thermocompression ratio of 3 to 35%.

4. The warmth-retaining cloth according to claim 1, wherein the fabric of the cover material is a woven fabric, a knitted fabric, a cheesecloth or an extruded mesh or net.

* * * * *